United States Patent [19]

Lowell, Jr. et al.

[11] Patent Number: 5,120,505
[45] Date of Patent: Jun. 9, 1992

[54] CHEMICAL SENSORS

[75] Inventors: James R. Lowell, Jr.; David J. Edlund; Dwayne T. Friesen, all of Bend; George W. Rayfield, Eugene, all of Oreg.

[73] Assignee: Bend Research, Inc., Bend, Oreg.

[21] Appl. No.: 724,123

[22] Filed: Jul. 1, 1991

Related U.S. Application Data

[63] Continuation-in-part of Ser. No. 509,012, Apr. 13, 1990, Pat. No. 5,028,394.

[51] Int. Cl.⁵ .................... G01N 19/00; G01N 19/10; G01N 27/00
[52] U.S. Cl. .................................... 422/58; 422/57; 422/82.01; 422/82.02; 422/82.05; 422/82.06; 436/150; 436/151; 436/164
[58] Field of Search ............... 422/57, 58, 68.1, 82.01, 422/82.02, 82.05, 82.06; 436/150, 151, 164; 73/23.2, 24.01, 24.06, 53, 775, 776

[56] References Cited

U.S. PATENT DOCUMENTS 5,015,843 5/1991 Seltz et al. .................... 250/227.21

Primary Examiner—Robert J. Warden
Assistant Examiner—Stephanie Blythe
Attorney, Agent, or Firm—Chernoff, Vilhauer, McClung & Stenzel

[57] ABSTRACT

Sensors responsive to small changes in the concentration of chemical species are disclosed, comprising a mechanicochemically responsive polymeric film capable of expansion or contraction in response to a change in its chemical environment, either operatively coupled to a transducer capable of directly converting the expansion or contraction to a measurable electrical or optical response, or adhered to a second inert polymeric strip, or doped with a conductive material.

32 Claims, 4 Drawing Sheets

CHEMICAL SENSORS

The government has rights in this invention pursuant to Contract No. DE-AC03-87ER80514 awarded by the Department of Energy and Contract No. 68D80070 awarded by the Environmental Protection Agency.

This is a continuation-in-part of application Ser. No. 509,012, filed Apr. 13, 1990, now U.S. Pat. No. 5,028,394.

BACKGROUND OF THE INVENTION

Fast and accurate monitoring of the pH and toxic metals content of industrial waste streams and of waterways has become a task of paramount importance in current efforts to maintain the quality of the environment. Commercially available sensors for toxic metal ions are limited to ion-selective electrodes (ISEs) for detecting Ag(I), Cd(II), Cu(II), and Pb(II). Such devices are based on a potentiometric measurement, and their accuracy is affected by numerous interfering agents. Furthermore, ISEs are fragile, respond slowly, can be used only in aqueous solutions, are subject to fouling, and require frequent calibration. For these reasons ISEs are not suitable for widespread use in pollution-control systems, and most operators must therefore rely on costly and time-consuming off-site laboratory analyses to determine if a waste stream or ground-water contains excessive levels of toxic materials. Belyakov, in 17 *Soviet Automatic Control* 34 (1984), discloses several theoretical sensors comprising fibers, granules or round polymer contractile films operatively coupled to mechanical transducers such as springs and pistons. In discussing the theoretical kinetics of such sensors, the author assumed that the analyte of interest carries no electrical charge.

For on-site control of waste discharge, ideally a sensor would be connected to an automatic flow shut-off valve in the effluent stream by a feedback control loop such that if levels of hydrogen or hydroxide ion or certain metals exceeded preset limits, the sensor would signal the valve to interrupt discharge, thus preventing excessive release to the environment. In cases where contamination of the environment had already occurred or was suspected of occurring, remotely placed sensors could be used to continuously monitor the groundwater to provide a detailed map of the extent of contamination. For such applications a sensor must be sensitive to the analyte, must respond quickly to changes in the analyte concentration, must have a relatively long life, and must not require frequent calibration. These needs are met by the chemical sensor of the present invention.

Many polymers are known to be capable of exhibiting a physical response, such as expansion or contraction, to a change in the polymer's chemical environment, such as a change in the concentration of a given chemical species, usually as a result of chemical or physical interaction with the species. This capability is often referred to as "mechanicochemical" responsiveness. Poly(methacrylic acid) (PMAA), cross-linked either with divinylbenzene or by esterification, is known to undergo volume expansions of up to 300% on conversion from the acid form to the polyanion form. Such expansion, which is reversible upon addition of mineral acid, has been explained on the basis of conformation changes in the polymer. The electrically neutral polyacid form consists of tightly coiled polymer chains. However, when the polymer is converted to the polyanion form, it has been theorized that electrostatic repulsion between negatively charged carboxylate groups results in full extension of the polymer chains and in the observed 300% expansion. See Kuhn et al., 7 *Experientia* 1(1951).

This expansion/contraction response of methacrylic acid polymer is not limited to the reaction with hydrogen and hydroxide ions. PMAA and poly(acrylic acid) (PAA) have been shown to form complexes with transition metal and alkaline earth cations. See Gregor et al., 59 *J. Phys. Chem.* 34 (1955). PAA complexed more strongly than did PMAA, and both formed stronger complexes than did glutaric acid, their monomeric analog. The complexation constant varied with the metal and its valence; transition metals generally yielded stronger complexes than did alkaline earth metals, and divalent and trivalent ions complexed more strongly than did monovalent valent ions. See Osada, 18 *J. Polym. Sci.* 281 (1980). The experimental results suggest that the complexes involve two carboxylate ions per metal ion over a wide range of pH values. See Mandel et al., 2 *J. Polym. Sci.* 2883 (1964 Part A). Crosslinked polymers formed weaker complexes than did linear polymers. Gregor et al., 59 *J. Phys. Chem.* 366 (1955). That the complexation of these metal ions by polycarboxylate anions involves a contractile response was demonstrated by the results of Osada, who used the same coiled-versus-extended-chain hypothesis to explain the increase in permeability observed in PMAA-grafted porous poly(vinyl alcohol) (PVA) membranes upon exposure to copper(II) salt solutions.

It has now been found that sensors for chemical species can be prepared by coupling a thin polymer film that undergoes a dimensional change in response to changes in the concentration of the species of concern, with any of an inert flexible polymer strip, an electrical transducer, or an optical transducer.

SUMMARY OF THE INVENTION

The present invention comprises a two-element chemical sensor consisting of a mechanicochemically responsive polymeric film capable of expansion or contraction in response to a change in its chemical environment, operatively coupled to a second element which may be either (a) a transducer capable of directly converting said expansion or contraction to a measurable electrical or optical response, or (b) an inert flexible polymer strip for direct measurement of the degree of said expansion or contraction.

DETAILED DESCRIPTION OF THE INVENTION

According to the present invention, there is provided a simple, economical, fast, accurate and reliable means of measuring changes in the concentration of chemical species in both aqueous and nonaqueous environments.

Figure 1A:
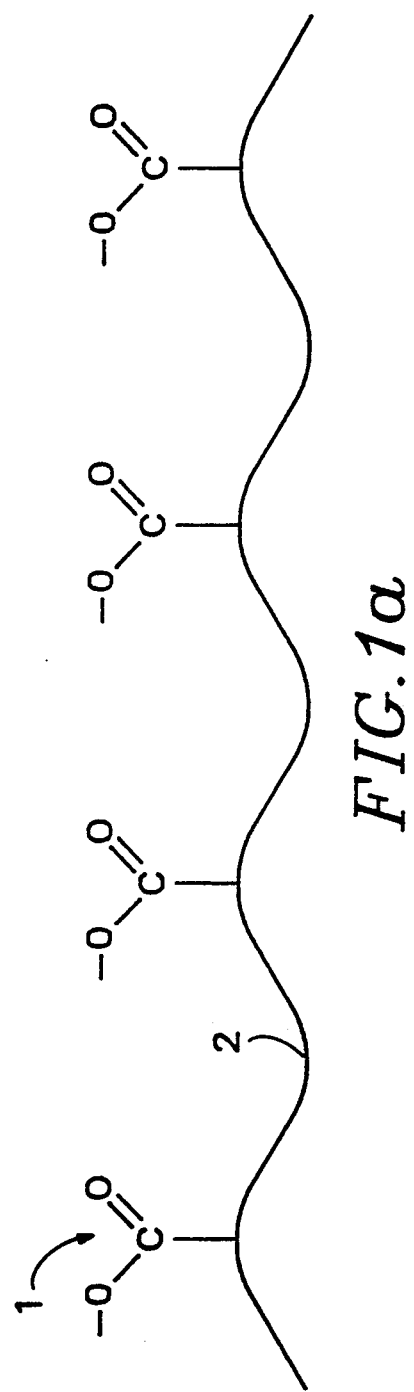
FIGS. 1a and 1b are schematic illustrations of an exemplary mechanicochemical response in a polymer film of the sensor of the present invention.
Figure 1B:
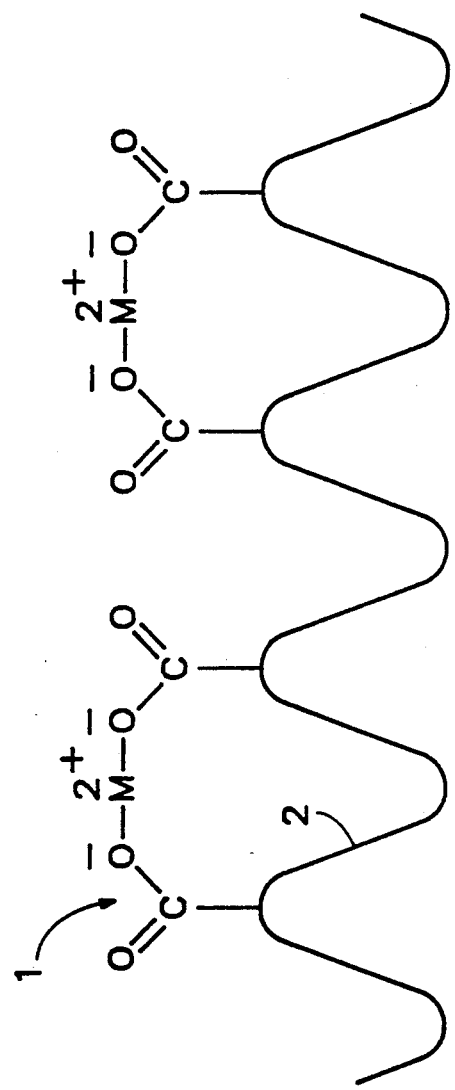

FIG. 1a shows a schematic of an exemplary mechanicochemically responsive polymeric film containing carboxylate functional groups 1 in pendant positions covalently bonded to the polymer backbone 2 prior to coordination with metal ions M. FIG. 1b shows the same film after coordination with metal ions, which causes a contraction of the film. Generally speaking, in order to be capable of an expansion or contractile response, the sensing element should be wettable by, and preferably swellable by, a solution of the analyte of interest. Other functional groups besides carboxylate that may be included in the mechanicochemically responsive sensing element portion of the sensor of the present invention include those that are capable of coordinating or otherwise interacting with hydrogen ions and weak acids, hydroxide ions and weak bases, metal ions or other analytes of interest. Such other functional groups include an aldehyde, an amine, an imine, an amide, an imide, a carbamate, an ester, an ether, a hydroquinone, a hydroxy, a ketone, a lactam, a lactone, a nitrile, a phosphate, a phosphine, a phosphite, a pyridine, an alkylated pyridine, a sulfone, a sulfoxide, a thiol, a thioamide, a thioester, a thioether, a thiourea, a urea, a urethane, and heterocycles containing oxygen, nitrogen or sulfur hetero atoms. The mechanicochemically responsive polymeric film may contain more than one species of functional group and, in this manner, may be "tuned" to fit a particular application where the presence of more than one chemical species is to be detected or, owing to the particular chemical environment, detection of the species of interest requires the presence of more than one type of functional group.

Although FIGS. 1a and 1b show the functional group 1 covalently bonded to the polymer backbone 2 in pendant positions, such functional groups may also be part of the repeating unit of the mechanicochemically responsive polymeric film or the polymeric film may be doped with the functional group(s). By "doped" is meant physically absorbed onto or into the mechanicochemically responsive polymeric film.

Particularly preferred sensing element polymers include polyethyleneimine (PEI), poly(acrylic acid) (PAA) and poly(alkylacrylic acid) such as poly(methacrylic acid) (PMAA). Crosslinking such polymers imparts resilience, durability and dimensional stability to the sensing element, and is preferably accomplished by conventional methods with 0.01 to 0.2 mol of cross-linking reagent per polymer repeating unit. Exemplary cross-linking reagents are polyamines such as ethylenediamine, diethylenetriamine, 1,6-hexanediamine and phenylenediamine; polyols such as glycerol, ethylene glycol, sorbitol, mannitol, scyllitol and inisotols (d-,l- and myo-); multifunctional acid halides such as adipoyl chloride, isophthaloyl chloride, malonyl chloride, terephthaloyl chloride and trimesoyl chloride; and multifunctional isocyanates such as tolylene diisocyanate (TDI), phenylene diisocyanate, methylene-bis-(phenylisocyanate) and poly[methylene-bis-(phenylisocyanate)]. In addition, grafted polymers having pendant functional groups such as carboxylate, amine, quaternary amine and sulfonate grafted to polymers such as polyethylene, polypropylene, polysulfone, polyethersulfone, polyamide, polyetherimide, polyester and poly(vinylidene fluoride) make desirable sensing elements for use in the sensors of the present invention. A preferred series of commercially available grafted polymers is the Raipore ® series from RAI Research Corporation of Long Island, N.Y., including Raipore ® ADM-4000 (a tertiary amine-grafted polyethylene), Raipore ® 5035 (a quaternized vinylbenzylamine-grafted polyethylene), Raipore ® R-1010 (a sulfonate-grafted polyethylene), and Raipore ® BDM-10 (a carboxylate-grafted polyethylene).

Figure 2:
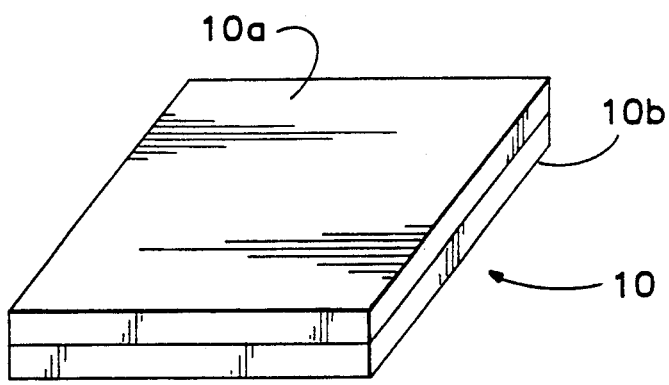
FIG. 2 is a schematic isometric drawing of an exemplary sensor of the present invention, consisting of a mechanicochemically responsive polymer film and an electrical transducer.

FIG. 2 shows a schematic of an exemplary sensor 10 comprising a mechanicochemically responsive polymeric film sensing element 10a and a transducer 10b. In general the sensing element portion 10a of the sensor should be fairly thin, on the order of 1–20 mils thick, in order to minimize the time required for diffusion of the analyte into the bulk of the sensing element and to maximize its flexibility and thus its ability to efficiently transfer expansion or contraction to the transducer 10b. Ideally, the sensing element should be integral with the transducer element, through fusing, adhesion or bonding with an adhesive between the sensing element and the transducer.

Conventional polymer fabrication methods may be used in preparing the sensing element; two methods are particularly preferred, i.e., casting and interfacial polymerization. One version of the casting method uses a solution of the desired polymer cast in a very thin film, which then is allowed to evaporate, depositing the polymer on the transducer support. Alternatively, a solution of complementary monomers may be cast as a thin film on the support. Polymerization of the monomers may then proceed spontaneously to be induced by removal of the solvent; e.g., azeotropic dehydration will tend to drive a condensation polymerization to completion by elimination of water. Both casting methods generally result in adhesion of the polymer film to the transducer support. In the interfacial polymerization technique, a thin film of a solution of a first reagent (a multifunctional monomer) is applied to the transducer support, then a second solution (in an immiscible solvent) of a monomer containing complementary functional groups that are reactive with the first reagent in a condensation reaction is applied to the support. Polymerization occurs at the interface between the two solutions to yield a very thin, defect-free film.

The fundamental requirement of the transducer element of the sensor is that it be capable of directly converting to a measurable electrical or optical response the expansion or contraction transmitted to it by the sensing element. Suitable transducers are strips of piezoelectric material and strain gauges, the latter including metal foil-types, semiconductor types and capacitance devices, as well as devices that utilize the principles of optics.

Figure 3A:
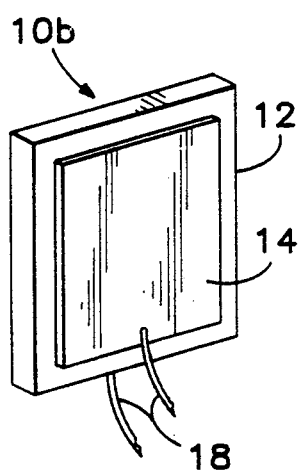
FIGS. 3a and 3b are schematic drawings of both sides of an exemplary polymeric piezoelectric transducer of the sensor of the present invention.
Figure 3B:
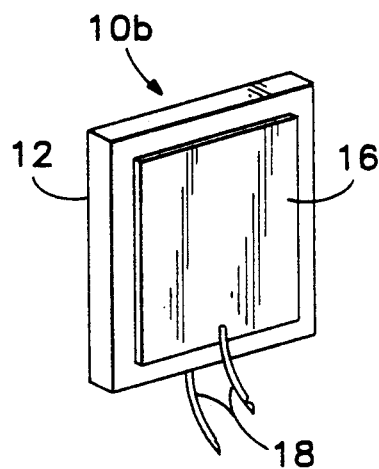

Piezoelectric materials are known to undergo a change in surface charge density upon deformation so that, in principle, if electrodes are attached to the two surfaces of a planar strip of such material, a measurable voltage occurs upon expansion or contraction of the material. Thus, if piezoelectric material is coupled to a mechanicochemically responsive analyte-sensitive element of the type described herein, a measurable voltage can be produced in response to a change in the concentration of an analyte of interest. A particularly preferred piezoelectric material is extruded and polarized poly(vinylidene fluoride) (PVDF) that is commercially available as "Kynar ®" from the Pennwalt Corporation of King of Prussia, Pa. After extrusion, the PVDF Kynar ® film contains nonpolar alpha- and polar beta-crystallite phases. The film is then stretched at 80° to 110° C., metallized with a conductive metal such as palladium or silver by vacuum deposition or screen printing, then polarized by subjecting it to an intense electric field at 80° to 100° C., followed by cooling it within the applied field. A schematic drawing of a Kynar ® piezoelectric transducer 10b is shown in FIGS. 3a and 3b as comprising a PVDF substrate 12 having a working electrode 14 on one side of the substrate and a common electrode 16 on the other side, and leads 18 for connection to an electrical response measuring device such as a voltmeter. Such a transducer may be modified to incorporate a reference electrode with the working electrode on the same side of the substrate; the signal from the reference electrode may be subtracted from the working electrode signal to remove background electrical noise from the sensor response.

Figure 6:
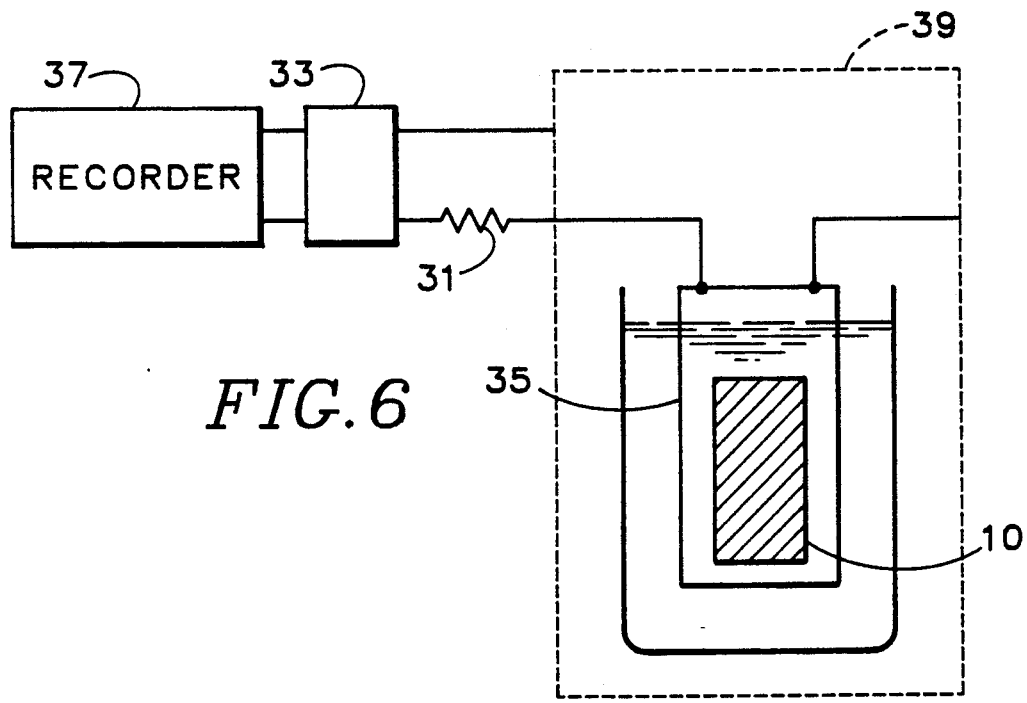
FIG. 6 is a schematic drawing of an exemplary electrical circuit for use in measuring changes in the resistance of a piezoelectric transducer of the present invention.

A circuit for measuring the voltage produced by the piezoelectric Kynar ® transducer is shown in FIG. 6. The large resister 31 ($10^8$ ohm) prevents the piezoelectric strip from discharging too rapidly. The 10× amplifier 33 simply amplifies the voltage produced by the piezoelectric sensor 10 immersed in analyte solution 35 to a value (0.1–10 V) that is conveniently displayed on a recorder 37. The entire circuit is placed in a Faraday cage 39.

Figure 4:
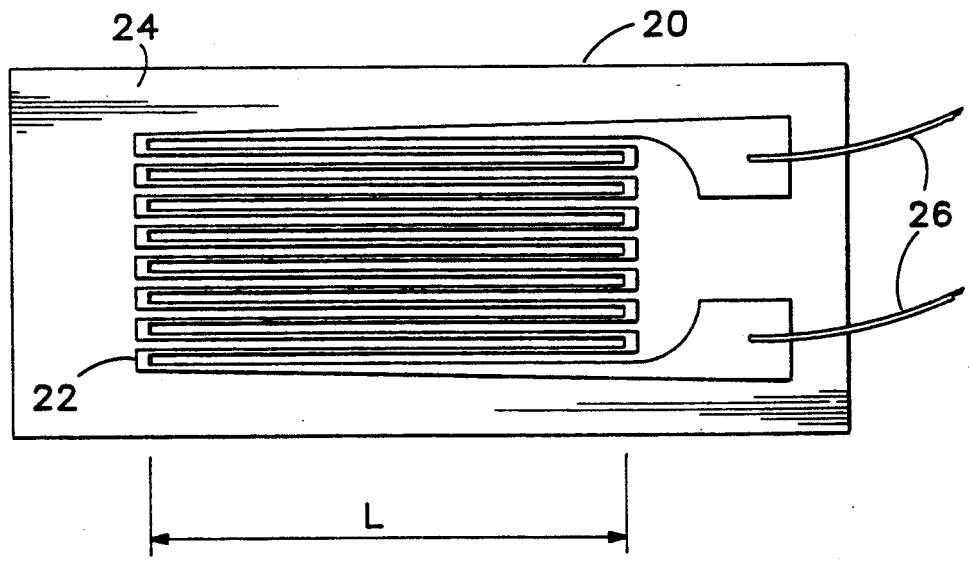
FIG. 4 is a schematic drawing of an exemplary metal foil strain gauge transducer of the sensor of the present invention.
Figure 7:
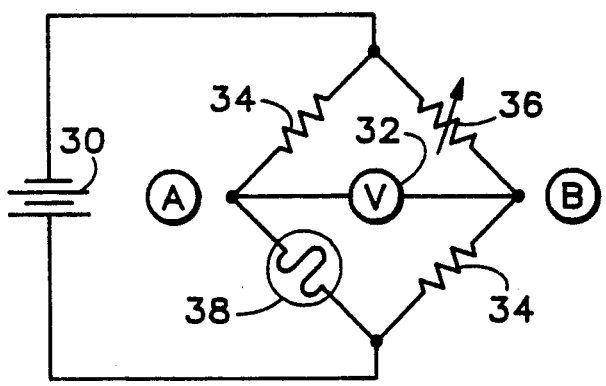
FIG. 7 is a schematic drawing of an exemplary Wheatstone bridge circuit for use in measuring changes in the resistance of a strain gauge transducer of the sensor of the present invention.

Strain gauges are well known and are preferably either of the thin metal foil type or the semiconductor type. A metal foil strain gauge is shown schematically in FIG. 4 as structure 20 having a serpentine conductive metal foil grid 22 on a nonconductive substrate 24, with leads 26 to the grid 22. When the strain gauge is expanded or contracted along the L axis, the electrical resistance of the grid will increase or decrease, respectively, according to the equation $$\Delta R/R = F(\Delta L/L)$$

where R is the initial resistance, R is the change in resistance, F is a dimensionless constant called the gauge factor, L is the initial length of the gauge, and $\Delta L$ is the change in the length of the gauge. Small changes in electrical resistance of such strain gauges are readily measured, for instance, with a Wheatstone bridge circuit, a simple form of which is pictured schematically in FIG. 7, wherein there is shown a DC power source 30, a DC voltmeter 32, fixed resistors 34, a variable resistor 36, and a strain gauge 38. The Wheatstone bridge circuit measures a small resistance change as an imbalance in the voltage potential between points A and B; the circuit derives its sensitivity from the fact that small potential differences between points A and B can be measured indirectly, but very precisely.

The semiconductor strain gauge is based on the piezoresistive effect in certain semiconductor materials such as silicon and germanium. Semiconductor gauges have elastic behavior and can be produced to have either positive or negative resistance changes when strained. They can be made physically small while still maintaining a high terminal resistance. Semiconductor gauges exhibit a high sensitivity to strain but the change in resistance with strain is nonlinear. Their resistance and output are temperature-sensitive and the high output, resulting from changes in resistance as large as 10–20%, can cause measurement problems when using the devices in a bridge circuit. However, mathematical corrections for the temperature sensitivity, the nonlinearity of output, and the nonlinear characteristics of the bridge circuit (if used), can be made automatically when using computer-controlled instrumentation to measure strain with semiconductor gauges. Both metal foil strain gauges and semiconductor strain gauges are commercially available from Omega Engineering of Stamford, Conn.

Another way in which electrical resistance may be used to transduce size changes in the mechanicochemically responsive polymeric film is by making the film itself electrically conductive by, for example, doping the film with a conductive substance such as powdered carbon or metal. Dimensional changes in the film will then produce a change in the film's resistance between two given points on the film, which variable resistance may in turn be measured in an analogous fashion to the strain gauge, discussed above.

Other examples of electrical properties which may be utilized to transduce size changes in the polymeric film sensor element include coupling the element to a solenoid or to a capacitor.

Figure 8:
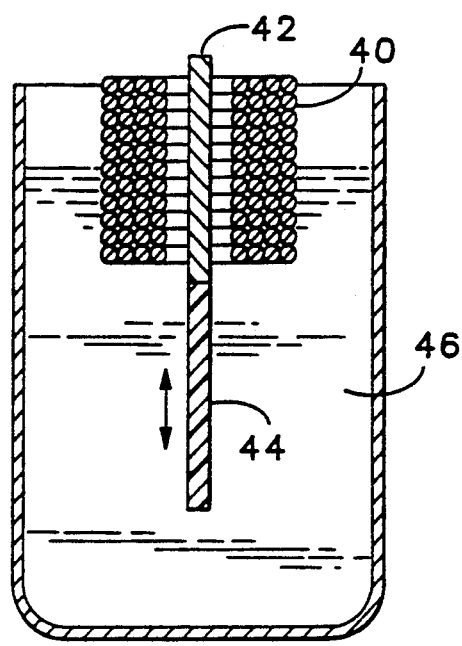
FIG. 8 is a schematic cross-sectional view of an exemplary linear voltage displacement transducer suitable for use with the sensor of the present invention.

The mechanicochemically responsive polymeric film may be attached by an adhesive to the iron core of a solenoid which is part of a linear voltage displacement transducer (LVDT), such as is shown schematically in cross-section in FIG. 8. The LVDT comprises a solenoid 40 with a movable iron core 42, the iron core being secured to the mechanicochemically responsive polymeric film 44 that is immersed in a solution 46 of the analyte of interest. Both the solenoid and core may be sealed to prevent contact with the solution. The inductance of the solenoid varies with the position of the iron core with respect to the solenoid. Movement of the core will result in a change in the inductance of the solenoid. Size changes of the sensing element 44 will cause the iron core of the solenoid to move, causing a change in inductance, which in turn may be measured by an inductance meter. Such LVDTs are commercially available from G. L. Collins Company of Long Beach, Calif.

The spacing between capacitor plates determines its capacitance. By placing the polymeric sensing element between the plates, dimensional changes in the sensing element may be made to vary the distance between the plates, which in turn will cause a change in capacitance of the capacitor which can be measured, using conventional impedance measuring techniques.

Optical responses may also be used to transduce the size changes of the polymeric sensing element of the present invention. Some examples follow.

Figure 9:
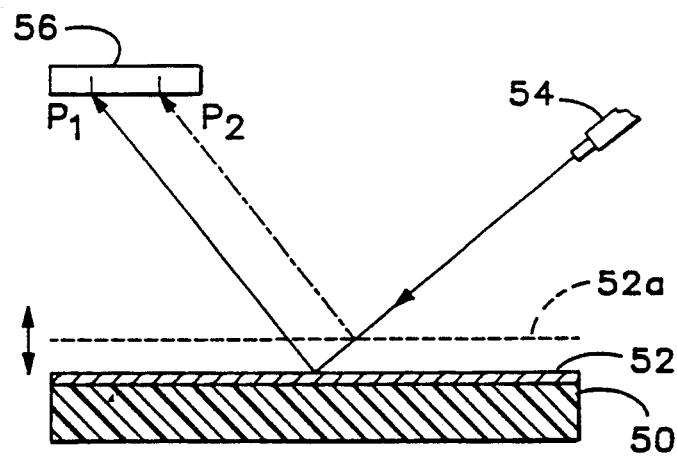
FIG. 9 is a schematic of an exemplary transducer which utilizes an optical response to transduce size changes in the polymeric sensing element of the present invention.

The direction in which light is reflected from a surface follows from the law of reflection. If the surface is moved (either rotated or translated), then the direction of the reflected light is changed. The reflecting surface such as a thin metal foil may be adhered to the polymeric sensing element by, for example, an adhesive. Size changes of the sensing element cause the reflecting surface to move. A single photodetector or a photodetector array may be used to determine the direction and degree of change in the reflected light. An exemplary arrangement is shown schematically in FIG. 9, where a mechanicochemically responsive polymeric film 50 is shown secured to a reflective foil 52. The surface of the reflective foil reflects light at a predetermined angle from a laser light source 54 and onto a light detector 56 capable of detecting changes on the order of a fraction of a micrometer in the apparent position of a light source. Such laser/light sensor optical devices are commercially available as Model No. LC-2100 from Keyence Corporation of Fairlawn, N.J. In operation, a laser beam striking the reflective layer 52 would be sensed by the light sensor 56 at $P_1$; upon expansion of the polymeric sensing element 50, the reflective layer would move upward to the dotted line 52a, and causing the laser beam to impinge upon the light sensor 56 at $P_2$, a change in the apparent position of the light source.

Figure 10:
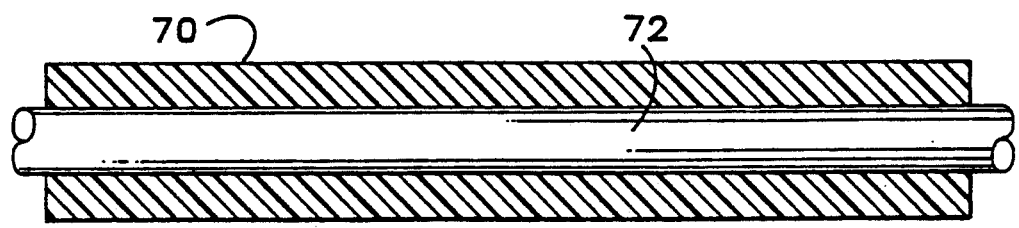
FIG. 10 is a schematic of still another exemplary optical transducer that uses an optical absorber such as a dye.

The intensity of a light beam depends on the amount of optical absorber in the path of the light beam. The amount of optical absorber may be altered simply by blanking out part of the light beam with opaque material such as is the case with an iris or shutter. The amount of optical absorber in the light path may also be changed by altering the amount of optical absorber in the evanescent wave of a fiber optic. An optical absorber such as an organic dye may be doped into the polymeric sensing element. Suitable organic dyes include Basic Red No. 9, Phenyl Red, Methyl Violet, Methyl Violet B, Methyl Orange and other azo dyes. Size- changes of the polymeric sensing element change the intensity of a light beam, which may be measured by a photodetector. An exemplary arrangement of this type is shown in FIG. 10 where a mechanicochemically responsive polymeric film sensing element 70 doped with an organic dye is shown as a coating around an optical fiber 72. The evanescent wave of the fiber optic 72 extends partly into the dye-doped polymeric sensing element 70 coating the surface of the fiber optic. The dye absorbs light in the evanescent wave. When the polymeric film expands, less of the dye is in the evanescent wave region, and therefore less light is absorbed, causing more light to travel down the fiber optic, the change in intensity of light in the fiber optic light beam being measurable by a photodetector.

Under appropriate conditions the expansion or contraction of the sensing element may be measured directly without the need for a transducer. For instance, the sensing element may be bonded by an adhesive to a flexible inert polymer film such as polyethylene of approximately the same thickness as the sensing element to form a composite bi-polymer strip. Upon exposure to a solution containing the analyte of interest, the sensing element would expand or contract, causing the composite polymer strip to curl in a fashion analogous to a bi-metallic strip for sensing changes in temperature. The degree of curl in the bi-polymer strip would be read directly from a scale precalibrated to relate the degree of deflection in the bi-polymer strip to the concentration of analytes, thereby providing a measure of the amount of analyte present in the sample solution.

In the Examples which follow, it should be noted that, in those cases where hydrogen ion concentration is measured in aqueous environments, hydroxide ion concentration is calculable from the mathematical relationship $[H^+][OH^-] = 10^{-14}$, and thus also measurable. In a nonaqueous environment, the sensor would have to be first calibrated by measuring the electrical response to known concentration of hydroxide ion.

EXAMPLE 1

A sensor that utilized a Kynar ® piezoelectric strip transducer of the type shown in FIGS. 3a and 3b was prepared by mixing 1.0 g (0.023 unit-mol, where a unit-mol is a gram-molecular-weight of a repeating monomer unit in a polymer solution) of poly(ethylenimine) (PEI) and 0.05 g ($2.9 \times 10^{-4}$ mol) of 2,4-tolylenediisocyanate (TDI) to produce a soft, gel-like polymer mixture. The gel was pressed onto a 28 micron-thick Kynar ® piezoelectric PVDF strip measuring $17 \times 40$ mm, after which the strip was heated at 90° to 95° C. until the PEI gel was quite stiff. Silver electrodes screen printed on each surface of the PVDF film permitted electrical connections to the sensor. Using a circuit of the type shown in FIG. 6, the so-fabricated sensor gave an electrical response comprising a voltage change ranging from 1500 mV to 3000 mV, when immersed in aqueous solutions of pH between 4 and 8.5, that was proportional to the change in pH, as shown in Table 1.

TABLE 1

| pH | Response (mV) |
| --- | --- |
| 8.0 | 3000 |
| 7.5 | 2550 |
| 6.5 | 2230 |
| 5.5 | 1920 |
| 4.5 | 1675 |
| 4.0 | 1500 |

EXAMPLE 2

A sensor was prepared by coating the same size and type piezoelectric strip as in Example 1 with a film of amide-cross-linked PMAA. A silicone rubber dam, capable of holding approximately 3 ml of liquid, was placed around the periphery of the piezoelectric strip. A 2 to 3 ml quantity of a 0.35 unit-molar aqueous solution of PMAA containing $1.7 \times 10^{-3}$ mol of 1,6-hexanediamine per liter and 0.1% poly(ethylene glycol) (PEG) was placed on the piezoelectric strip inside the dam. The water was evaporated at 90° to 95° C., resulting in the formation of a thin amide-cross-linked PMAA film on the piezoelectric strip. Using the same type of measuring device as in Example 1, the so-fabricated sensor gave an electrical response ranging from 250 mV at pH 6.5 to 860 mV at pH 2.5 when immersed in acetonitrile solutions of HCl, as shown in Table 2.

TABLE 2

| pH* | Response (mV) |
| --- | --- |
| 6.5 | 250 |
| 5.5 | 350 |
| 4.5 | 750 |

TABLE 2-continued

| pH* | Response (mV) |
|---|---|
| 3.5 | 825 |
| 2.5 | 860 |

*Calculated

EXAMPLE 3

A hydrogen ion sensor was prepared in the same manner as in Example 2 by coating the same size and type of piezoelectric-film transducer with the polymer formed in nitromethane solution by reaction of the acid chloride of PMAA with glycerol. The response to changes in hydrogen-ion concentration in nonaqueous (acetonitrile) solutions with this sensor was similar to the response of the sensor of Example 2, as shown in Table 3.

TABLE 3

| pH* | Response (mV) |
|---|---|
| 6.5 | 250 |
| 5.5 | 350 |
| 4.5 | 750 |
| 3.5 | 825 |
| 2.5 | 860 |

*Calculated

EXAMPLE 4

The PMAA-coated sensor of Example 2 was also responsive to changes in the concentration of Cu(II) in aqueous solutions thereof (in the form of $CuSO_4$), as shown in Table 4.

TABLE 4

| [Cu(II)] (ppb) | Response (mV) |
|---|---|
| 0.6 | 50 |
| 6.0 | 100 |
| 60 | 200 |
| 600 | 500 |
| 60,000 | 1300 |

EXAMPLE 5

The PMAA-coated sensor of Example 3 was identically responsive to changes in the concentration of aqueous Cu(II) as was the sensor of Example 2.

EXAMPLE 6

The PMAA-coated sensor of Example 2 was also responsive to changes in the concentration of Cr(III) in aqueous solutions thereof (in the form of $CrCl_3$), as shown in Table 5.

TABLE 5

| [Cr(III)] (ppb) | Response (mV) |
|---|---|
| 2.6 | 50 |
| 26 | 60 |
| 260 | 130 |
| 2600 | 260 |
| 26,000 | 710 |

EXAMPLE 7

The PMAA-coated sensor of Example 3 was identically responsive to changes in the concentration of aqueous Cr(III) as was the sensor of Example 3.

EXAMPLE 8

A sensor prepared in substantially the same manner as in Example 1 with the TDI-crosslinked PEI being doped after heating by the addition of 0.1 to 0.3 ml of the beta-diketone LIX 860 to the surface of the sensor, the doping agent being absorbed into the mechanicochemically responsive polymer film. This sensor was responsive to changes in the concentration of Fe(II) and Fe(III) in aqueous solutions thereof (in the form of $FeSO_4 \cdot (NH_4)_2SO_4 \cdot 6H_2O$ and $FeCl_3$, respectively). As shown in Table 6 the sensor was much more responsive to Fe(III) than to Fe(II).

TABLE 6

| Metal Ion | [M] (ppm) | Response (mV) |
|---|---|---|
| Fe(II) | 780 | 400 |
| Fe(III) | 780 | 1200 |

EXAMPLE 9

The PEI-coated sensor of Example 1 was also responsive to changes in the concentration of Cr(III) in aqueous solutions thereof (in the form of $CrCl_3$), as shown in Table 7.

TABLE 7

| [Cr(III)] (ppb) | Response (mV) |
|---|---|
| 260 | 100 |
| 2600 | 275 |
| 26,000 | 450 |

EXAMPLES 10–26

Figure 5:
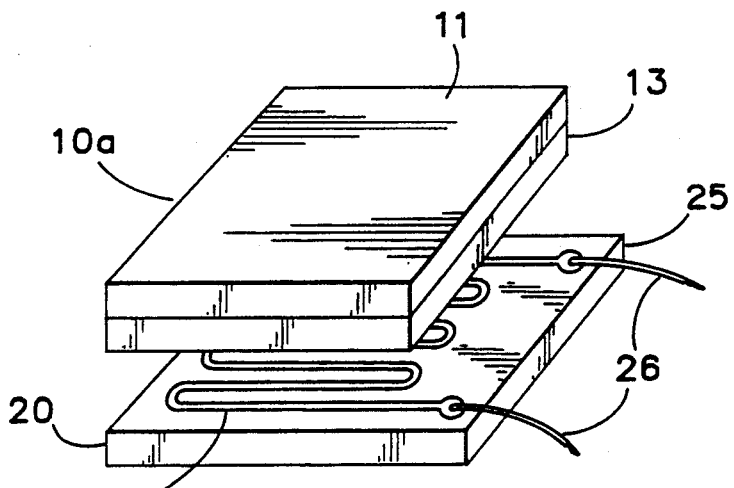
FIG. 5 is a schematic exploded view of an exemplary sensor, of the present invention, comprising a mechanicochemically responsive polymer film and a strain gauge transducer.

Sensors of substantially the design shown in FIG. 5 were prepared by bonding 2×2 cm pieces of carboxylate- and tertiary amine-grafted polyethylene films 11 2 mil-thick (Raipore ® BDM-10 and ADM-4000, respectively) to metal foil strain gauge transducers 20 that had been prepared by sputtering a Pd/Au alloy in a 5×1.5 cm serpentine grid pattern 22 onto 2 mil-thick 2×2 cm sheets of polyurethane 25 and attaching thin copper wire leads 26 to each end of the grid with conductive silver epoxy. Bonding was accomplished by first applying a thin coating of amine functional group-containing silicone polymer 13 (GP-134 by Genesee Polymers Corp. of Flint, Mich.) to the Raipore ® polymer film, allowing it to cure, swelling it in water, blotting it dry, coating it with a general purpose silicone adhesive, and then joining the Raipore ® polymer film 11 to the strain gauge transducer 20. A Wheatstone bridge circuit of the type shown in FIG. 7 was used to detect changes in the resistance of the strain gauge, expressed as a voltage imbalance in the circuit. Size changes of the Raipore ® polymer films varied from about 0.5% to about 15.5%, in response to changes in the concentration of the metal ions Ba(II), Cd(II), Cr(III) and Cr(VI) in the form of aqueous solutions of $BaCl_2$, $CdSO_4$, $CrCl_3$ and $Na_2CrO_4$. Raipore ® BDM-10 films were used in connection with measuring the concentration of all ions except Cr(VI), in which case Raipore ® ADM-4000 was used.

The variance of the electrical response with metal ion concentration was as shown in Table 8.

TABLE 8

| Ex. No. | Metal Ion | [M] (ppm) | Response (mV) |
|---|---|---|---|
| 10 | Ba(II) | 13 | 1.1 |
| 11 | " | 10 | 0.98 |
| 12 | " | 7.0 | 0.74 |
| 13 | " | 3.5 | 0.54 |
| 14 | " | 0.7 | 0.04 |
| 15 | Cd(II) | 5.5 | 0.35 |
| 16 | " | 3.0 | 0.21 |
| 17 | " | 1.2 | 0.09 |
| 18 | " | 0.6 | 0.05 |
| 19 | Cr(III) | 2.0 | 0.96 |
| 20 | " | 1.0 | 0.65 |
| 21 | " | 0.5 | 0.47 |
| 22 | " | 0.03 | 0.40 |
| 23 | Cr(VI) | 20 | 0.26 |
| 24 | " | 15 | 0.19 |
| 25 | " | 10 | 0.17 |
| 26 | " | 5.0 | 0.10 |

Based upon the results shown in Table 8, the calculated limits of detection of the sensors of Examples 10-26 are shown in Table 9.

TABLE 9

| Analyte | Limits of Detection (ppm) | |
|---|---|---|
| | Minimum | Maximum |
| Ba(II) | 0.67 | >13.4 |
| Cd(II) | 0.56 | >5.6 |
| Cr(III) | 0.025 | >2.0 |
| Cr(VI) | 5.0 | >20.0 |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A chemical sensor consisting essentially of a mechanicochemically responsive polymeric film capable of dimensional expansion or contraction in response to a change in its chemical environment, said film being doped with an electrically conductive material.

2. A chemical sensor consisting essentially of (a) a mechanicochemically responsive polymeric film capable of dimensional expansion or contraction in response to a change in its chemical environment mechanically coupled to (b) a linear voltage displacement transducer.

3. A chemical sensor consisting essentially of (a) mechanicochemically responsive polymeric film capable of dimensional expansion or contraction in response to a change in its chemical environment adhered to (b) an inert flexible polymeric strip.

4. A chemical sensor consisting essentially of (a) mechanicochemically responsive polymeric film capable of dimensional expansion or contraction in response to a change in its chemical environment adhered to (b) a reflective film that is interposed between a laser beam source and a photodetector capable of detecting changes in the apparent position of said laser beam source of less than a micron 5. A chemical sensor consisting essentially of (a) mechanicochemically responsive polymeric film capable of dimensional expansion or contraction in response to a change in its chemical environment adhered to (b) an optical fiber, said polymeric film being doped with a light-absorbing dye.

6. The sensor of claim 1, 2, 3, 4 or 5 wherein said mechanicochemically responsive polymeric film contains at least one functional group being selected from an aldehyde, an amine, an imine, an amide, an imide, a carbamate, a carboxylate, an ester, an ether, a hydroquinone, a hydroxy, a ketone, a lactam, a lactone, a nitrile, a phosphate, a phosphine, a phosphite, a pyridine, an alkylated pyridine, a sulfone, a sulfoxide, a thiol, a thioamide, a thioester, a thioether, a thiourea, a urea, a urethane, and heterocycles containing oxygen, nitrogen or sulfur hetero atoms.

7. The sensor of claim 6 wherein said mechanicochemically responsive polymer film is doped with said at least one functional group.

8. The sensor of claim 6 wherein said at least one functional group is covalently bonded to the polymer backbone of said mechanicochemically responsive polymeric film.

9. The sensor of claim 8 wherein said at least one functional group is in pendant positions on said polymer backbone.

10. The sensor of claim 8 wherein said at least one functional group is part of the repeating unit of said polymer backbone.

11. The sensor of claim 1, 2, 3, 4 or 5 wherein said mechanicochemically responsive polymeric film is selected from polyethyleneimine, poly(acrylic acid) and poly(alkylacrylic acid).

12. The sensor of claim 1, 2, 3, 4 or 5 wherein said mechanicochemically responsive polymeric film is cross-linked with 0.01 to 0.2 mol cross-linking reagent per polymer repeating unit.

13. The sensor of claim 12 where said cross-linking reagent is selected from the group consisting of a polyamine, a polyol, an acid chloride and an isocyanate.

14. The sensor of claim 13 wherein said cross-linking reagent is a polyamine and said polyamine is selected from the group consisting of ethylenediamine, diethylenetriamine, hexamethylenediamine, 1,6-hexanediamine and a phenylenediamine.

15. The sensor of claim 13 wherein said cross-linking reagent is a polyol and said polyol is selected from the group consisting of glycerol, ethylene glycol, sorbitol, mannitol, scyllitol and inisotols.

16. The sensor of claim 13 wherein said cross-linking reagent is a acid chloride and said acid chloride is selected from the group consisting of adipoyl chloride, isophthaloyl chloride, malonyl chloride, terephthaloyl chloride and trimesoyl chloride.

17. The sensor of claim 13 wherein said cross-linking reagent is an isocyanate and said isocyanate is selected from the group consisting of tolylene diisocyanate, a phenylene diisocyanate, methylene bis-(phenylisocyanate) and poly[methylene bis-(phenylisocyanate)].

18. The sensor of claim 1, 2, 3, 4 or 5 wherein said mechanicochemically responsive polymer film comprises a functional group-grafted copolymer wherein the functional group is selected from carboxylate, sulfonate and amine.

19. The sensor of claim 18 wherein the polymer to which said functional group is grafted is selected from polyethylene, polypropylene, poly(vinyl-idenefluoride) and polysulfone.

20. The sensor of claim 1, 2, 3, 4 or 5 wherein the change in chemical environment is a change in hydrogen ion concentration.

21. The sensor of claim 1, 2, 3, 4 or 5 wherein the change in chemical environment is a change in the concentration of a weak acid.

22. The sensor of claim 1, 2, 3, 4 or 5 wherein the change in chemical environment is a change in hydroxide ion concentration.

23. The sensor of claim 1, 2, 3, 4 or 5 wherein the change in chemical environment is a change in the concentration of a weak base.

24. The sensor of claim 1, 2, 3, 4 or 5 wherein the change in chemical environment is a change in transition metal ion concentration.

25. The sensor of claim 24 wherein the transition metal ion is Cd(II).

26. The sensor of claim 24 wherein the transition metal ion is Cr(III).

27. The sensor of claim 24 wherein the transition metal ion is Cr(VI).

28. The sensor of claim 24 wherein the transition metal ion is Cu(II).

29. The sensor of claim 24 wherein the transition metal ion is Fe(II).

30. The sensor of claim 24 wherein the transition metal ion is Fe(III).

31. The sensor of claim 24 wherein the mechanicochemically responsive polymeric film is doped with a beta-diketone.

32. The sensor of claim 1, 2, 3, 4 or 5 wherein the change in chemical environment is a change in Ba(II) concentration.

* * * * *

UNITED STATES PATENT AND TRADEMARK OFFICE
CERTIFICATE OF CORRECTION

PATENT NO. : 5,120,505

DATED : June 9, 1992

INVENTOR(S) : James R. Lowell, Jr., et al.

It is certified that error appears in the above-identified patent and that said Letters Patent is hereby corrected as shown below:

Col. 10, line 47: delete "5 X 1.5" insert --1.5 X 1.5--.

Signed and Sealed this

Thirty-first Day of August, 1993

Attest:

BRUCE LEHMAN

*Attesting Officer*      *Commissioner of Patents and Trademarks*